(12) United States Patent
Vollmer et al.

US009493819B2

(10) Patent No.: US 9,493,819 B2
(45) Date of Patent: Nov. 15, 2016

(54) SENSOR DEVICE AND METHOD FOR LABEL-FREE DETECTING OF NUCLEIC ACID SEQUENCES

(71) Applicants: Frank Vollmer, Fuerth (DE); Yuqiang Wu, Erlangen (DE); David Zhang, Houston, TX (US)

(72) Inventors: Frank Vollmer, Fuerth (DE); Yuqiang Wu, Erlangen (DE); David Zhang, Houston, TX (US)

( * ) Notice: Subject to any disclaimer, the term of this patent is extended or adjusted under 35 U.S.C. 154(b) by 0 days.

(21) Appl. No.: 14/341,973

(22) Filed: Jul. 28, 2014

(65) Prior Publication Data
US 2015/0147756 A1 May 28, 2015

Related U.S. Application Data

(60) Provisional application No. 61/862,225, filed on Aug. 5, 2013.

(51) Int. Cl.
| | |
|---|---|
| *C12M 1/34* | (2006.01) |
| *C12Q 1/68* | (2006.01) |
| *C07H 21/02* | (2006.01) |
| *C07H 21/04* | (2006.01) |
| *C40B 30/04* | (2006.01) |
| *G01N 31/22* | (2006.01) |
| *G01N 33/52* | (2006.01) |
| *G02B 26/00* | (2006.01) |
| *G02B 17/00* | (2006.01) |

(52) U.S. Cl.
CPC ........... *C12Q 1/6825* (2013.01); *G02B 17/004* (2013.01); *G02B 26/001* (2013.01)

(58) Field of Classification Search
CPC .................. C12Q 1/68; G02B 6/29341; C40B 20/06; G01N 33/52
USPC ......... 435/6.1, 287.2; 536/23.1, 24.3; 506/9; 422/430
See application file for complete search history.

(56) References Cited

U.S. PATENT DOCUMENTS

2010/0041030 A1* 2/2010 Hartwich ............. C12Q 1/6834
435/6.11

OTHER PUBLICATIONS

Vollmer, F. et al., "Review Label-free detection with high-Q microcavities: a review of biosensing mechanisms for integrated devices," Nanophotonics 1, 267-291 (2012).
Fan, X. D. et al., "Sensitive optical biosensors for unlabeled targets: A review," Anal. Chim. Acta 620, 8-26 (2008).
Qavi, A. J. et al., "Label-free technologies for quantitative multiparameter biological analysis," Anal. Bioanal. Chem. 394, 121-135 (2009).
Hunt, H. K. et al., "Label-free biological and chemical sensing," Nanoscale 2, 1544-1559 (2010).
Vollmer, F. et al., "Whispering-gallery-mode biosensing: label-free detection down to single molecules," Nat. Methods 5, 591-596 (2008).
Yoshie, T. et al., "Optical Microcavity: Sensing down to Single Molecules and Atoms," Sensors 11, 1972-1991 (2011).
Lin, S. Y. et al., "Planar silicon microrings as wavelength multiplexed optical traps for storing and sensing particles," Lab Chip 11, 4047-4051 (2011).
Lu, T. et al., "High sensitivity nanoparticle detection using optical microcavities ," Proc. Natl. Acad. Sci. U. S. A. 108, 5976-5979 (2011).
Lopez-Yglesias, X. et al., "The physics of extreme sensitivity in whispering gallery mode optical biosensors," J. Appl. Phys, 111 (2012).
Vollmer, F. et al., "Single virus detection from the reactive shift of a whispering-gallery mode ," Proc. Natl. Acad. Sci. U. S. A. 105, 20701-20704 (2008).
Qavi, A. J. et al., "Multiplexed detection and label-free quantitation of MicroRNAs using arrays of silicon photonic microring resonators," Angew. Chem.-Int. Edit. 49, 4608-4611 (2010).
Nakatani, K. et al., "Chemistry Challenges in SNP Typing," Chembiochem 5, 1623-1633 (2004).
Vollmer, F. et al., "Multiplexed DNA Detection by Optical Resonances in Microspheres," Biophys. J. 85, 1974-1979 (2003).
Qavi, A. J. et al., "Isothermal discrimination of single-nucleotide polymorphisms via realtime kinetic desorption and label-free detection of DNA using silicon photonic microring resonator arrays," Anal. Chem. 83, 6827-6833 (2011).
Suter, J. D. et al. et al., "Label-free quantitative DNA detection using the liquid core optical ring resonator," Biosens. Bioelectron. 23, 1003-1009 (2008).
Lee, M. et al., "A fiber-optic microarray biosensor using aptamers as receptors," Anal. Biochem. 282, 142-146 (2000).
Zhang, D. Y. et al., "Optimizing the specificity of nucleic acid hybridization," Nat. Chem. 4, 208-214 (2012).
Yin P et al, "Programming biomolecular self-assembly pathways," Nature 451, 318-323, 2008.
Li, B. L. et al., "Mobilization of giant piggyBac transposons in the mouse genome," Nucleic Acids Res. 39 (2011).
Zhang, D. Y. et al., "Engineering Entropy-Driven Reactions and Networks Catalyzed by DNA," Science 318, 1121-1125 (2007).
Zhang, D.Y. et al., "Dynamic DNA nanotechnology using strand-displacement reactions," Nat. Chem. 3, 103-113 (2011).
Zhang, D.Y. et al., "Control of DNA strand displacement kinetics using toehold exchange," J. Am. Chem. Soc. 131, 17303-17314 (2009).

* cited by examiner

*Primary Examiner* — Narayan Bhat
(74) *Attorney, Agent, or Firm* — 24IP Law Group; Timothy R DeWitt

(57) ABSTRACT

A sensor device, which is adapted for detecting target molecules having a target nucleic acid sequence, comprises an optical whispering gallery mode (WGM) resonator having a resonance frequency, wherein the WGM resonator is functionalized with a double-strand DNA precursor compound and the resonance frequency depends on a mass load provided by the double-strand precursor compound, the double-strand precursor compound is capable of a target-specific strand displacement reaction with the target molecules, and in response to the strand displacement reaction, the double-strand precursor compound is capable to be partially decoupled from the WGM resonator, wherein the mass load can be decreased and the resonance frequency of the WGM resonator can be increased. Furthermore, a sensing method for detecting target molecules including nucleic acid sequences is described.

7 Claims, 4 Drawing Sheets

SENSOR DEVICE AND METHOD FOR LABEL-FREE DETECTING OF NUCLEIC ACID SEQUENCES

CROSS-REFERENCE TO RELATED APPLICATIONS

The present application claims the benefit of the filing date of U.S. Provisional Patent Application Ser. No. 61/862,225 filed by the present inventors on Aug. 5, 2013.

The aforementioned provisional patent application is hereby incorporated by reference in its entirety.

STATEMENT REGARDING FEDERALLY SPONSORED RESEARCH OR DEVELOPMENT

None.

SEQUENCE LISTING

The instant application contains a Sequence Listing which has been submitted electronically in ASCII format and is hereby incorporated by reference in its entirety. Said ASCII copy, created on Feb. 10, 2015, is named 13081.1629-4655_SL.txt and is 4,147 bytes in size.

BACKGROUND OF THE INVENTION

1. Field of the Invention

The present invention relates to a sensor device for label-free detecting nucleic acid sequences, comprising an optical whispering gallery mode (WGM) resonator. Furthermore, the present invention relates to a sensing method for label-free detecting nucleic acid sequences using the WGM resonator. Applications of the invention are available e.g. in the fields of research and clinical nucleic acid sequence detection or screening.

2. Brief Description of the Related Art

It is generally known that specific detection of nucleic acids, like DNA and RNA, is an important research and clinical goal as nucleic acids act to encode and regulate the expression of genes. Conventional detection techniques are based on detecting label or marker substances, or they use label-free sensors.

Label-based sensors use, e.g., fluorescence-based assays to localize and quantitate nucleic acid molecules of interest. However, functionalizing oligonucleotides with fluorescent labels is typically a complex and expensive process that often skews physical and chemical properties, in turn affecting quantitative readout. Label-free sensors circumvent the need for fluorescence modifications, and they are based on, e.g., detecting plasmon resonance, electrochemical conductance or mechanical resonance. However, these techniques may have disadvantages in terms of limited sensitivity or specificity, e.g., due to limited kinetics and thermodynamics of direct hybridization at stringent conditions.

A promising label-free sensor comprises an optical whispering gallery mode (WGM) resonator. See, Vollmer, F. et al., Nanophotonics 1, 267-291 (2012); Fan, X. D. et al., Anal. Chim. Acta 620, 8-26 (2008); Qavi, A. J. et al., Anal. Bioanal. Chem. 394, 121-135 (2009); Hunt, H. K. et al., Nanoscale 2, 1544-1559 (2010); Vollmer, F. et al., Nat. Methods 5, 591-596 (2008); Yoshie, T. et al., Sensors 11, 1972-1991 (2011).

WGM resonators are micron scale optical cavities, such as glass microspheres, capable of confining light by total internal reflection in a small modal volume and only at specific resonance frequencies (resonance wavelengths). These tiny optical resonators exhibit ultra-narrow linewidth, associated with very high quality Q factor, and are extremely sensitive to the binding of biomolecules to the microcavity resonator surface. The changes in permittivity upon binding of analyte result in a shift of the resonance frequency. The high Q factor enables the precise monitoring of small resonance frequency shifts, a method known as the reactive biosensing principle. Vollmer, F. et al., Nanophotonics 1, 267-291 (2012). With the conventional WGM resonator, the resonance frequency is decreased depending on an increasing mass load in response to a specific binding reaction with a target molecule under investigation. The target molecule can be detected by monitoring the negative frequency shift. Optical WGM sensors are emerging as one of the most versatile and sensitive label-free detecting techniques, providing various mechanisms for sensing, sizing, trapping, and manipulation down to the nanoscale. Vollmer, F. et al., Nanophotonics 1, 267-291 (2012); Lin, S. Y. et al., Lab Chip 11, 4047-4051 (2011); Lu, T. et al., Proc. Natl. Acad. Sci. U.S.A. 108, 5976-5979 (2011); Lopez-Yglesias, X. et al., J. Appl. Phys, 111 (2012).

Advantageously, WGM sensors are simple to fabricate, can be functionalized as well as multiplexed, and are made from inexpensive optical fibers. See, Fan, X. D. et al., Anal. Chim. Acta 620, 8-26 (2008); Hunt, H. K. et al., Nanoscale 2, 1544-1559 (2010); Yoshie, T. et al., Sensors 11, 1972-1991 (2011); Vollmer, F. et al., Proc. Natl. Acad. Sci. U.S.A. 105, 20701-20704 (2008); and Qavi, A. J. et al., Angew. Chem.-Int. Edit. 49, 4608-4611 (2010). However, as a general disadvantage, sequence-specific detection by direct DNA hybridization on WGM sensor devices, faces three important challenges: limited sensitivity, specificity, and reusability. See, Fan, X. D. et al., Anal. Chim. Acta 620, 8-26 (2008); Qavi, A. J. et al., Angew. Chem.-Int. Edit. 49, 4608-4611 (2010); Nakatani, K. et al., Chembiochem 5, 1623-1633 (2004); Vollmer, F. et al., Biophys. J. 85, 1974-1979 (2003); Qavi, A. J. et al., Anal. Chem. 83, 6827-6833 (2011); and Suter, J. D. et al. et al., Biosens. Bioelectron. 23, 1003-1009 (2008).

First, years of work on advancing the device physics and engineering of WGM sensors has improved the ultimate physical detection limits of WGM transducers, yet the limits for DNA detection by hybridization has plateaued. Novel molecular approaches are needed to overcome those limitations, mostly set by the inherent kinetics and thermodynamics of the process of molecular recognition through direct hybridization at the sensor surface.

Second, label-free sensors based on hybridization struggle with single base specificity and SNP detection, due to the thermodynamic favorability of hybridization of non-cognate analytes with highly similar sequence to that of the analyte. Although specificity for any particular nucleic acid analyte/ probe pair can be optimized by solution salinity and temperature, this process is time consuming and imperfect, and not conducive to significant multiplexing. Similarly, the suppression of nonspecific interactions is essential to multiplexed detection. Thus, non-cognate sequences that differ slightly in sequence may bind non-specifically to the functionalized surface of conventional sensors, generating false positive signals and preventing proper detection.

Finally, conventional label-free nucleic acid detection technologies based on hybridization suffer from the limitation that a different functionalized device is needed to detect each different sequence. Furthermore, each device can generally be only used once; dehybridizing oligonucleotides requires harsh buffer conditions, high temperature, or practically takes too long. See, Lee, M. et al., Anal. Biochem. 282, 142-146 (2000). Thus, different sensors must be constructed to detect different nucleic acid sequences.

DNA strand displacement techniques have recently emerged as a novel family of approaches to enzyme-free homogenous detection assays. See, Zhang, D. Y. et al., Nat. Chem. 4, 208-214 (2012); Yin, P. et al., Nature 451, 318-U314 (2008); Li, B. L. et al., Nucleic Acids Res. 39 (2011); and Zhang, D. Y. et al., Science 318, 1121-1125 (2007). Strand displacement circuits, for example, have been demonstrated to implement nucleic acid "catalysis" in which a nucleic acid sequence of interest effects the release of up to 100 nucleic acid molecules from metastable precursors; cascading such catalytic systems has shown overall turnover of about 1000. Recently, strand displacement has been engineered to allow ultraspecific hybridization assays with specificity approaching the theoretical limit based on thermodynamics. Although strand displacement techniques have significantly improved the specificity and sensitivity of homogeneous detection assays, the readout for this technology has previously been constrained to gel electrophoresis or fluorescence readout, neither of which is easily applicable to point-of-care or clinical diagnostics. See, Zhang, D. Y. et al., Nat. Chem. 4, 208-214 (2012); Zhang, D. Y. et al., Science 318, 1121-1125 (2007); Zhang, D. Y. et al., Nat. Chem. 3, 103-113 (2011); and Zhang, D. Y. et al., J. Am. Chem. Soc. 131, 17303-17314 (2009).

SUMMARY OF THE INVENTION

An objective of the invention is to provide an improved sensor device for detecting nucleic acid sequences avoiding limitations of conventional techniques. In particular, an objective of the invention is to provide a sensor device having an increased specificity, sensitivity and/or reusability. Furthermore, an objective is to provide an improved sensing method for detecting nucleic acid sequences avoiding limitations of conventional techniques.

According to a first general aspect of the invention, the above objective is solved by a sensor device, which is adapted for detecting (sensing) target molecules having a target nucleic acid sequence, comprising an optical whispering gallery mode (WGM) resonator with a functionalized resonator surface which is adapted for a target-specific strand displacement reaction. The WGM resonator is a compact, mirror-free resonator accommodating a circulating light field having a resonance frequency, such as a microdisc, microsphere, microtoroid or microring. The WGM resonator is functionalized with a precursor compound, which can be partially unloaded by the target-specific strand displacement reaction. Unloading of the functionalized WGM resonator surface results in a reduction of the effective resonator size, e.g. diameter, associated with an increasing resonance frequency (decreasing resonance wavelength). Thus, according to the invention, the WGM resonator is adapted for providing an increasing resonance frequency in response to a mass load reduction resulting from the strand displacement reaction of the target molecule with the precursor compound. The target molecule can be detected by monitoring a positive resonance frequency shift. Preferably, the precursor compound is a double-strand DNA precursor compound which is capable of the strand displacement reaction with the target molecules. In response to the strand displacement reaction, the double-strand precursor compound is capable to be partially decoupled from the WGM resonator, so that the mass load can be decreased and the resonance frequency of the WGM resonator can be increased.

According to a second general aspect of the invention, the above objective is solved by a sensing method for detecting target molecules having nucleic acid sequences, wherein a sample liquid to be investigated is applied to a WGM resonator of the sensor device according to the above first aspect of the invention, a resonance frequency of the WGM resonator is measured and the target molecules are detected in the sample liquid if the resonance frequency of the WGM resonator is increased in response to the contact of the sample liquid with the WGM resonator. The target molecule to be detected comprises any molecule (biomolecules) which includes at least one nucleic acid sequence and which is capable of a hybridization reaction with a nucleic acid strand. The target molecule consists of one single nucleic acid sequence to be detected (target nucleic acid sequence), or it has multiple nucleic acid sequences including the target nucleic acid sequence.

Advantageously, the invention provides a nucleic acid detection with a label-free sensor which circumvents costly fluorophore functionalization steps associated with conventional assays by utilizing impressive ultimate detection limits provided by the WGM resonator. Despite this technological progress, molecular recognition at the WGM resonator surface is based on partial unloading of the precursor compound. The inventors have found that the concept of a DNA strand displacement reaction can be applied with a WGM sensor. Contrary to conventional WGM resonator based sensors, the target molecule is not bound to the resonator, but used for unloading the surface functionalization precursor molecules. This allows overcoming limits as to the sensors' sensitivity, specificity, and reusability.

With the invention, the advantages of WGM resonator label-free readouts and DNA strand displacement circuits are combined by constructing an integrated label-free sensor. The integrated sensor is highly specific, able to distinguish single nucleotide polymorphisms (SNPs) via kinetics of mass loading/unloading by a factor of 32 to 690.

Advantageously, various types of strand displacement reactions can be used with the invention. According to a first variant, a single replacement scheme is used wherein each target molecule to be detected is capable of releasing one strand from one precursor compound molecule. This variant has advantages in terms of a simple replacement reaction. According to a second, preferred variant, a catalytic replacement scheme is used wherein each target molecule to be detected is capable of releasing multiple strands from multiple precursor compound molecules. With this variant, a cyclic catalytic reaction pathway is obtained and the sensitivity of the detection can be essentially increased.

With the single replacement scheme of the first variant, the double-strand precursor compound has a primary strand and a secondary strand being hybridized with the primary strand, wherein the secondary strand is connected with the WGM resonator. The double-strand precursor compound can be partially decoupled from the WGM resonator by replacing the secondary strand by the target nucleic acid sequence and dissociating the primary strand hybridized with the target nucleic acid sequence from the WGM resonator. In other words, the double-strand precursor compound is selected such that the target nucleic acid sequence is capable of the replacement hybridization reaction with the primary strand. The replacement hybridization is energetically preferred compared with the initial hybridization of the primary and secondary strands. Thus, the target nucleic acid sequence specifically replaces the secondary strand. As the primary strand is connected to the WGM resonator via the secondary strand only, this replacement releases the primary strand from the WGM resonator, resulting in the mass load reduction to be obtained.

With the catalytic replacement scheme, the double-strand precursor compound has a primary strand and first and secondary strands being hybridized with the primary strand, wherein the first secondary strand is connected with the WGM resonator. The double-strand precursor compound can be partially decoupled from the WGM resonator by replacing the second secondary strand by the target nucleic acid sequence and by replacing the first secondary strand by a further single-strand precursor molecule (so called fuel strand), so that the primary strand hybridized with the target nucleic acid sequence and the single-strand precursor molecule is dissociated (separated) from the WGM resonator.

Advantageously, this integrated sensor adapted for the catalytic replacement scheme exhibits at least 25-fold improvement in molecular sensitivity over the conventional hybridization-based WGM nucleic acid sensor, thus allowing a detection of 80 pM (32 fmol) of a 22 oligomer. This improvement results from both the catalytic behavior of the functionalized WGM resonator and a decoupling of mass loading from the analyte. Furthermore, the integrated sensor exhibits extremely high specificity, discriminating single nucleotide polymorphisms by a factor of 32 to 690.

According to a particularly preferred embodiment of the catalytic replacement scheme, the single-strand precursor molecule is capable to replace the target nucleic acid sequence from the primary strand, so that the target molecule is directly released from the primary strand into the sample liquid to be tested. Thus, the repeated use of the target molecule for unloading primary strands from the WGM resonator is possible.

According to a preferred embodiment of the invention, the WGM resonator has a surface layer made of a biotin streptavidin compound to which the double-strand precursor compound, in particular the secondary strand (single replacement scheme) or the first secondary strand (catalytic replacement scheme) is coupled.

According to a further advantageous embodiment of the invention, the WGM resonator is provided in contact with at least one optical waveguide or optical prism. One single optical waveguide or prism can be arranged for both of in-coupling sample light (excitation light) into the WGM resonator and out-coupling resonator light out of the WGM resonator. Alternatively, a first optical waveguide or prism can be arranged for in-coupling the sample light, while a second optical waveguide or prism can be arranged for out-coupling the resonator light. Preferably, the at least one optical waveguide or optical prism is connected with the resonator surface.

The sample light (test light) is preferably generated with a continuous wave tunable laser source. The laser source is tuned to the resonance frequency of the WGM resonator loaded with the double-strand precursor compound. The resonator light is the light field resonantly circulating within the WGM resonator. If the target molecule to be detected is present in a sample liquid and the double-strand precursor compound is partially dissociated from the WGM resonator, the resonance frequency of the resonator light is increased compared with the frequency of the sample light. This positive frequency shift generally can be detected e.g. by spectrally resolved measuring the resonator light and comparing it with the spectrum of the sample light.

According to a further advantageous embodiment of the invention, the sensor device further comprises a sample cell being adapted for arranging the WGM resonator and accommodating the sample liquid to be investigated. Preferably, optical waveguides are arranged for carrying the sample light and the resonator light to and from the WGM resonator, resp., in the sample cell. The sample cell may comprise a substrate carrying a frame, like an O ring, accommodating a droplet of the sample liquid, wherein the WGM resonator can be arranged above the frame so that the WGM resonator contacts the sample liquid. Alternatively, the sample cell may comprise a container (vessel) enclosed with container walls. With this embodiment, the optical waveguides pass through the container walls. Using the container cell may have advantages in terms of providing a compact sensor structure which is adapted for point-of-care-uses.

In summary, for real-time, label-free nucleic acid detection, the inventive sensor device provides three major advantages over conventional label-free biosensor approaches: molecular sensitivity, molecular specificity, and device reusability. Experimentally, at least 25-fold enhancement of the sensitivity and detection down to about 80 pM (32 fmol) of a 22-mer DNA oligo, SNP discrimination by a factor of 32 to 690, and versatile detection by the same physical microsphere of 2 different analytes over 5 cycles of use have been shown. Discrimination against SNP variants of the intended analyte has been found to be robust to position and base identity of the SNP.

The versatility and reusability of the inventive sensor device show that the invention is suitable not only for laboratory investigations but also for real-world diagnostic applications. By allowing the same type of DNA-functionalized microsphere to be generally used for the detection of any nucleic acid biomarker, device manufacturing costs are sharply reduced. By allowing the same physical microsphere device to be used across multiple cycles of operation, the number of devices needed by the end-users is reduced. Consequently, the application of inventive sensor device to point-of-care diagnostics is facilitated.

BRIEF DESCRIPTION OF THE DRAWINGS

Further details and advantages of the invention are described in the following with reference to the attached drawings, which show in.

DETAILED DESCRIPTION OF THE PREFERRED EMBODIMENTS

Figure 3:
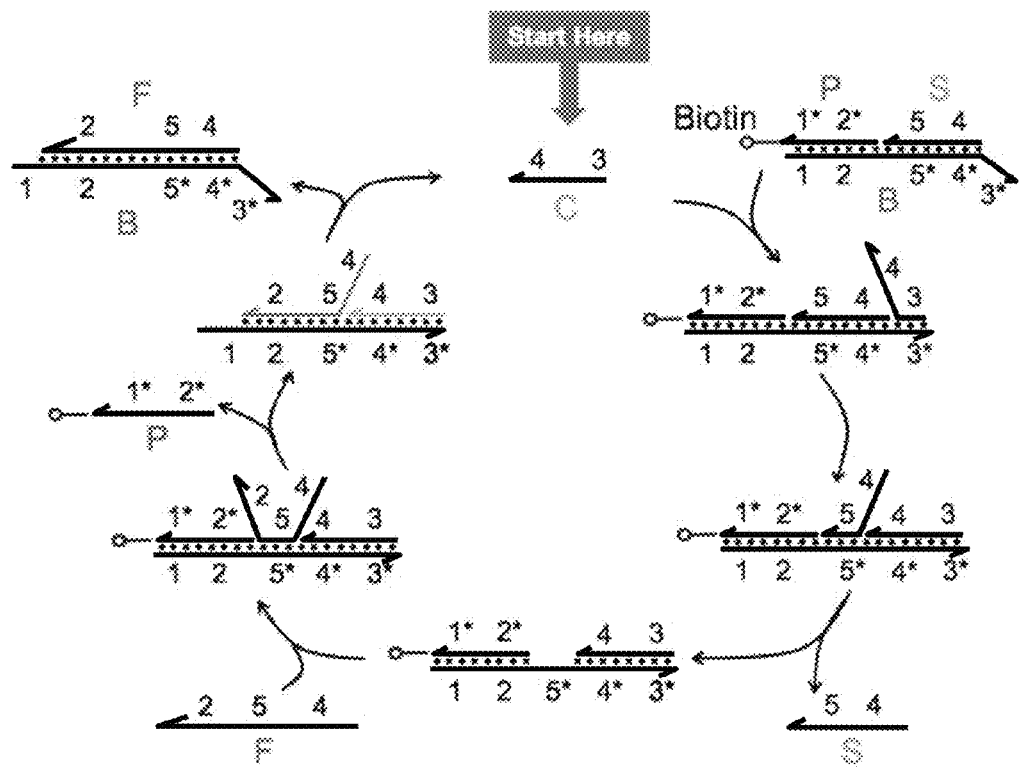
FIG. 3 is an illustration of a catalytic replacement scheme according to a preferred embodiment of the invention.
Figure 8:
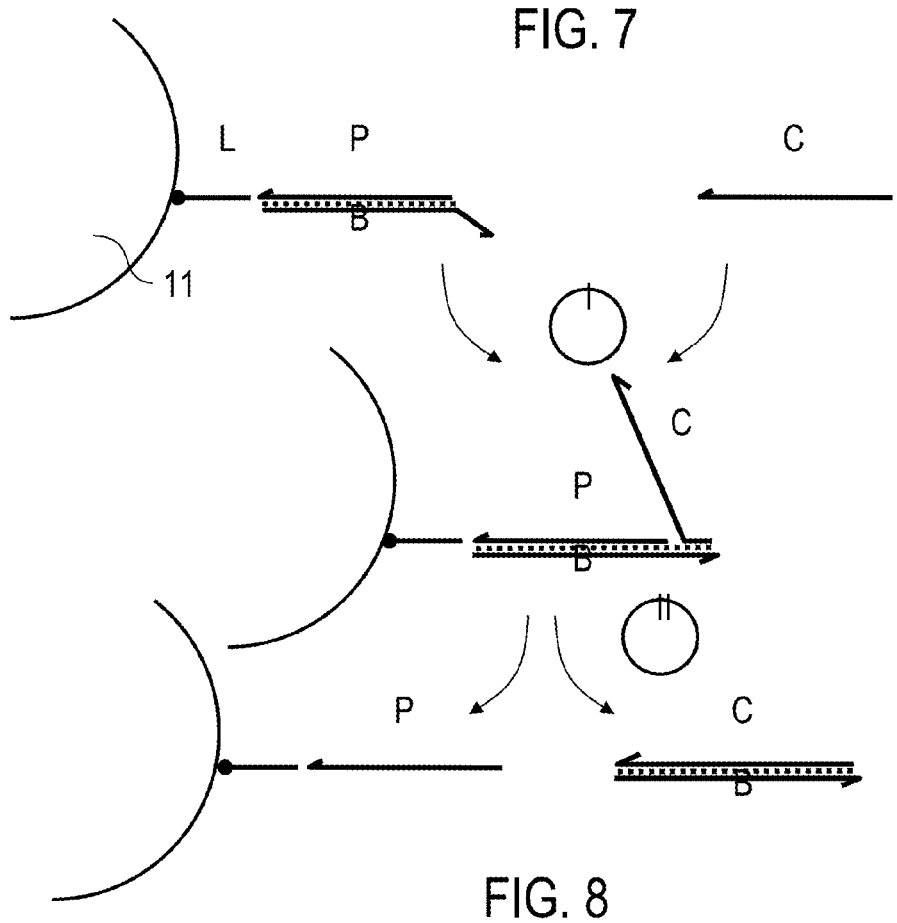
FIG. 8 is an illustration of a single replacement scheme according to a further embodiment of the invention.

Preferred embodiments of the invention are described in the following with reference to the design of a sensor device configured for detecting target nucleic acid sequences according to the invention and with reference to the concept of strand displacement reactions used for detecting target nucleic acid sequences. Details of operating a laser source, detecting resonator light and measuring light wavelengths/frequencies, and providing samples, in particular preparing nucleic acid sequences, are not described as far as they are known as such from prior art. Detailed reference is made to the catalytic replacement scheme of a strand displacement reaction, which represents a preferred embodiment of the invention (FIG. 3). However, implementing the invention is not restricted to this scheme but also possible with the single replacement scheme described below (FIG. 8). Exemplary reference is made to biotin-streptavidin linkers functionalizing the WGM resonator of the sensor device. The invention is not restricted to the use of these linkers but also possible with other linker molecules, e.g. heterobifunctional linkers, such as those based on amino and carboxy groups activated by EDC/NHS Esters, homobifunctional linkers, such as those based on thiol groups. Furthermore, instead of physisorbing dextran to immobilize the linker groups on the microsphere surface, the glass microsphere may also be conveniently modified with silane agents to introduce functional groups, e.g., using silanes which carry the amine linker or other linker groups. Finally, practical selection of double-strand precursor compounds and fuel molecules can be done by the skilled person in dependency on the hybridization properties of the target molecule to be detected.

Sensor Device

Figure 1:
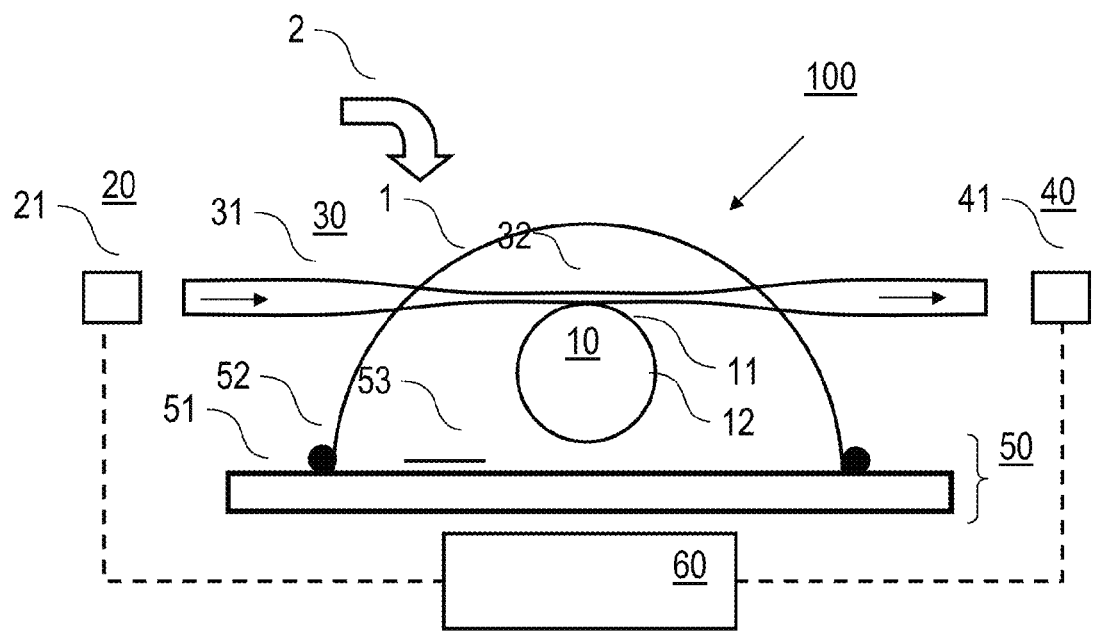
FIG. 1 is a schematic illustration of a sensor device according to a preferred embodiment of the invention.

Preferred features of an inventive sensor devices are described in the following with reference to FIGS. 1 and 2. The sensor device 100 comprises an optical WGM resonator 10, a light source device 20, an optical waveguide 30, a detector device 40, a sample cell 50 and a control device 60.

The WGM resonator 10 comprises a microsphere 11 having a functionalized surface 12. The microsphere 11 is made of silica, and it is fabricated e.g. by melting the tip of a short piece of optical fiber (e. g. SMF-28) with an oxygen-butane microtorch so that surface tension in the melted glass tip forms the silica microsphere having a 300 µm to 400 µm diameter. The microsphere-on-a-stem is mounted on a microstage (not shown) for controlled coupling to the optical waveguide 30. For specific DNA detection, the surface 12 of the microsphere 11 is functionalized with biorecognition elements, like e.g. a 22 mer DNA oligonucleotide (see below, FIGS. 3 and 4).

The light source device 20 includes a laser source 21, preferably a continous wave (cw) laser, like e.g. a tunable distributed feedback laser (DFB) laser operating at a wavelength of about 1550 nm. The laser source 21 can be scanned through a wavelength range including the resonance frequency of the WGM resonator 10, e.g. every millisecond to obtain a transmission spectrum of the WGM resonator 10 with a spectral width of about 0.2 nm.

Sample light (excitation light) from the laser source 21 is coupled via an imaging optic (e. g. a lens optic, not shown) into the optical waveguide 30, which comprises an optical fibre 31 with a tapered fiber region 31. The taper is fabricated e.g. from a single mode SMF-28 fiber using a microtorch to heat and at the same time pull apart the fiber. The microsphere 11 and the tapered fiber region 31 are arranged such that sample light can be coupled into the microsphere 11 by evanescent coupling.

The detector device 40 is arranged for detecting light output from the optical fibre 31 of the optical waveguide 30. The light output includes sample light and resonator light evanescently coupled out of the microsphere 11. The detector device 40 includes e.g. a photodiode 41. Spectra are recorded and processed using e.g. a commercial software, like LabVIEW. With a practical example, transmission spectra of the WGM resonator 10 are acquired by the photodiode 41 in real time while rapidly sweeping the laser source 41 wavelength by about 0.2 nm.

The sample cell 50 comprises a substrate 51, like a glass slide, and a frame 52, e. g. made of an O ring. The frame 52 is glued to the substrate 51, and it has a height of e. g. . . . 2 mm. Inside the sample cell 50, a miniature magnetic stir bar 53 is placed to homogenize the reactions. A droplet 1 of sample liquid 2 to be investigated is accommodated in the sample cell 50 by capillary forces. The droplet 1 has a volume of e.g. about 400 µl. After providing the droplet 1, e.g. using a pipette, the fiber-coupled microsphere 11 is immersed in the sample liquid. Alternatively, sample liquid 2 is added to droplet 1 to final volume e.g. about 400 µl.

The control device 60 is arranged for controlling the light source device 20 and the detector device 40 and for processing the spectra collected with the detector device 40. Optionally, the microstage of the microsphere 11, the magnetic stir bar 53 and/or further operation components of the sensor device 100 can be controlled as well. Furthermore, the control device 60 is adapted for analyzing the spectra collected with the detector device 40 and for providing an output indicating the detection of a target molecule. The control device 60 comprises e.g. a computer unit.

For implementing the inventive sensing method for detecting target nucleic acid sequences, the WGM resonator 10 is functionalized with a double-strand precursor compound and arranged in the sample cell 50. With a practical example of a DNA detection according to the invention, the double-strand precursor compound comprises single-stranded DNA oligonucleotide probes which are attached via biotin streptavidin linkers to a dextran hydrogel that is coated onto the silica microsphere by physisorption. See, Vollmer, F. et al., Biophys. J. 85, 1974-1979 (2003). Commercially available DNA oligonucleotides and standard procedures for purifying them can be used.

With more details, the microsphere 11 is functionalized e.g. with the following procedure. The microsphere 11 is cleaned in an air oxygen plasma for 5 minutes immediately after fabrication, then immersed in a 2 µl hanging drop of a dextran-biotin solution (10 mg/ml, Life Technologies) until almost dry. After a brief rinse in water for 5 min, it is then incubated until almost dry in a hanging drop of 2 µl of 8 µM solution of biotinylated DNA oligonucleotides (C* or P, see table below), coupled to streptavidin at a molar ratio of about 2:1. After incubation, the sphere is rinsed again in the water and stored there until use. The dextran hydrogel coating is preferred for functionalizing the WGM resonator 10 since it prevents unspecific binding of DNA and supports a high surface density of attached biotin molecules that link to biotinlyated oligonucleotides via streptavidin. A surface density of e.g. about $10^{13}/cm^2$ for biotin-streptavidinlinked DNA oligonucleotides can be obtained.

In an initial phase of the inventive sensing method, the sample cell 50 includes a sample-free liquid, like water. The transmission spectrum of the WGM resonator 10 is measured as a reference. Subsequently, the sample liquid to be investigated is contacted with the WGM resonator, e.g. by supplying to the sample cell 50. The hybridization or dissociation of oligonucleotides with partial or full complementarity to these probes induces a mass change which can be observed from resonance wavelength shift. Changes of transmission spectrum resulting from unloading the precursor compound from the surface 12 of the microsphere 11 are monitored. An increasing resonance frequency shows the presence of the target molecule in the sample liquid.

Figure 2:
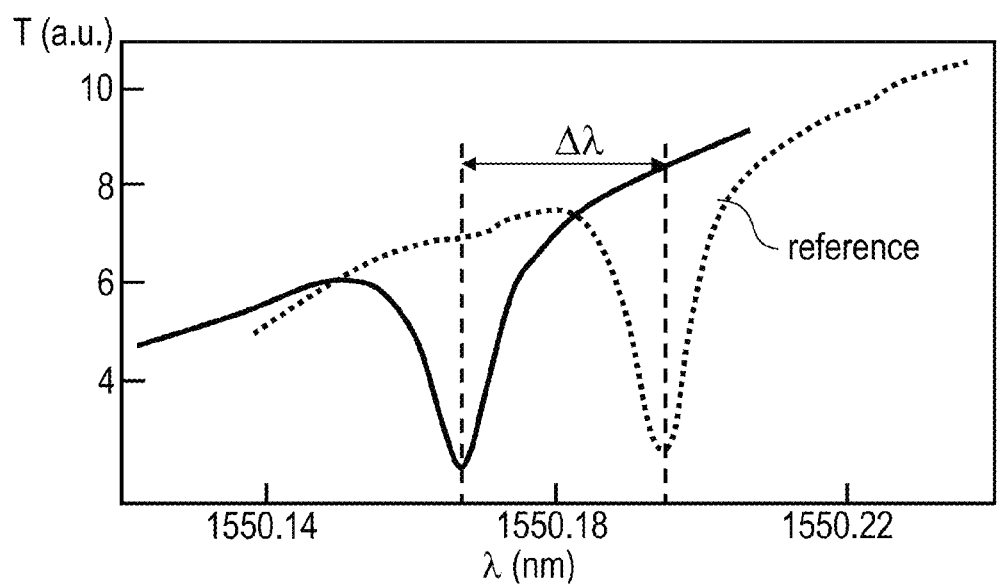
FIG. 2 is a graphical illustration of a positive frequency shift measured with a sensor device according to FIG. 1.

Typical spectra of the microsphere 11, here before (dotted line, reference) and after (solid line) the unloading of precursor compound from the surface 12 of the microsphere 11 are shown in FIG. 2. The resonance wavelength shift of the sensor device 100 (FIG. 1), for example upon DNA hybridization, is quantitated in grams of nucleic acid mass loading per millimeter-squared sensor area, pg/mm$^2$ (see, Baaske, M. et al., ChemPhysChem 13, 427-436 (2012) and Arnold, S. et al., Optics Letters 28, 272-274 (2003)):

$$massloading = \frac{\Delta\lambda(n_s^2 - n_m^2)R}{\lambda 2n_m \cdot \frac{dn}{dc}}$$

where $\Delta\lambda$ is the shift of resonance wavelength, $\lambda$ is the nominal wavelength of the laser source 21, $n_s$=1.46 and $n_m$=1.33 are the refractive indices of microsphere 11 and aqueous medium in the droplet 1, respectively, R is the approximate radius of the microsphere 11 as determined by microscopic imaging, and dn/dc~0.17*10$^{-9}$ [mm$^3$/pg] is the approximate incremental refractive index change of a DNA solution.

Catalytic Replacement Scheme of Strand Displacement Reaction

Figure 4:
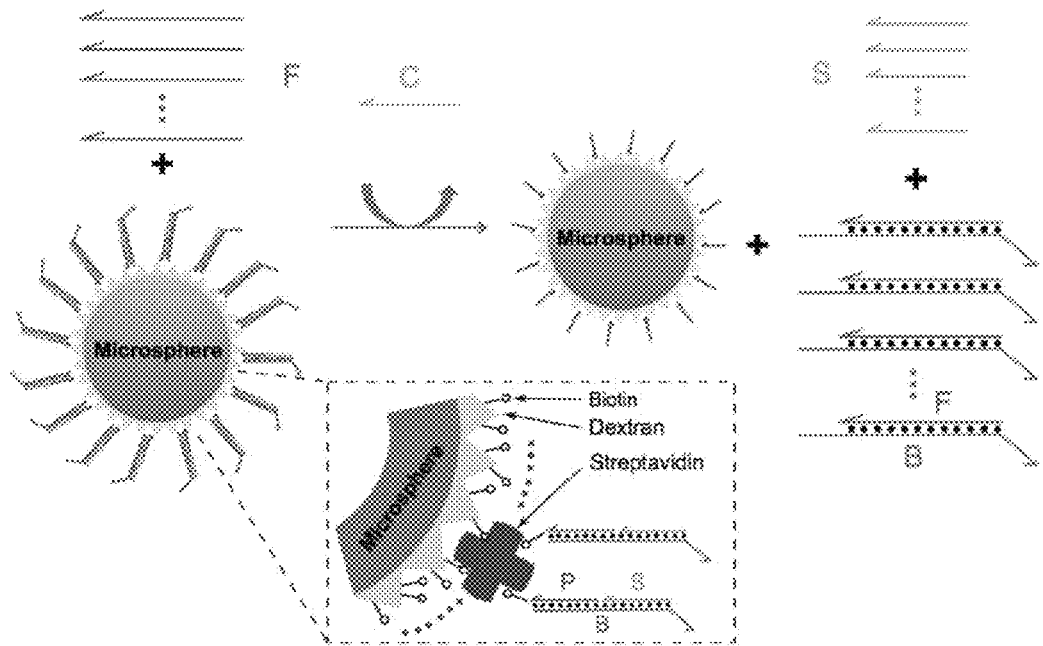
FIG. 4 illustrates further details of the catalytic replacement scheme according to FIG. 3.

For illustrating the catalytic replacement scheme according to a preferred embodiment of the invention, reference is made to FIGS. 3 and 4. Start step (step I) of FIG. 3 schematically shows the double-strand precursor compound SBP with a primary strand B and first and second secondary strands P, S being hybridized with the primary strand B, a target nucleic acid sequence C (analyte C) to be detected, and a fuel strand F (single-strand precursor molecule). The first secondary strand P is connected via a biotin molecule L with the microsphere 11 (see FIG. 4, insert). Examples of the molecules used for practically testing the inventive device are summarized in the following table:

| Domain | Sequences | SEQ ID NO: | Length (nt) |
|---|---|---|---|
| C | 5'-ATCAATC CTTCTCGTTTATCTC-3' | 1 | 22 |
| C* | 5'-biotin-GAGATA AACGAGAAG GATTGAT-3' | 2 | 22 |
| S | 5'-CTTCTCGTTTATCTCCTGTA-3' | 3 | 20 |
| B | 5'-GCGATG GGTAAGAACTTTAGTG TACAG GAGATAAACGAGAAG GATTGAT-3' | 4 | 49 |
| F | 5'-CTTCTCGTTTATCTC CTGTA CACTAAAGTTCTTACC-3' | 5 | 36 |
| P | 5'-CACTAAAGTTCTTACC CATCG-biotin-3' | 6 | 21 |
| Cm5aG | 5'-ATCAGTC CTTTCTCGTTTATCATC-3 | 7 | 22 |
| Cm11cT | 5'-ATCAATC CTTTTCGTTTATCTC-3' | 8 | 22 |
| Cm14gC | 5'-ATCAATC CTTCTCCTTTATCTC-3' | 9 | 22 |
| Fn | 5'-CTGTA CACTAAAGTTCTTACC-3' | 10 | 21 |
| C2 | 5'-TGTAACAGCAACTCCATGTGGA-3' | 11 | 22 |
| S2 | 5'-GCAACTCCATGTGGACTGTA-3' | 12 | 20 |
| B2 | 5'-GCGATG GGTAAGAACTTTAGTG TACAG TCCACATGGAGTIEGC TGTTACA-3' | 13 | 49 |
| F2 | 5'-GCAACTCCATGTGGA CTGTA CACTAAAGTTCTTACC-3' | 14 | 36 |
| T | 5'-CCCTATAGTGAGTCGTATTAAT-3' | 15 | 22 |
| T* | 5'-biotin-ATTAATACGACTCACTATAGGG-3' | 16 | 22 |

The two precursor molecules, F and SBP, are selected based on the sequence of the target nucleic acid sequence C to be detected.

In the absence of C, SBP is double-stranded everywhere it is complementary to F, so no significant reaction occurs, and the two species are metastable (see FIG. 4, left side). In the presence of the target nucleic acid sequence C, the second secondary strand S and the primary strand B are delocalized from P and the surface of the microsphere 11 as follows. The target nucleic acid sequence C acts catalytically to enable the reaction between SBP and F, resulting in the release of S and B from P. Domains (displayed as numbers in FIG. 3) represent continuous subsequences of nucleic acids that act as a unit in hybridization and dissociation; dotted domains are complementary to non-dotted domains.

The second secondary strand S is replaced by target nucleic acid sequence C (step II), wherein S is released into the surrounding liquid. Subsequently, the fuel strand F replaces the first secondary strand S (step III), so that the primary strand B with the fuel strand F and the target nucleic acid sequence C are decoupled from the microsphere 11 (step IV). Finally, the fuel strand F completely replaces the target nucleic acid sequence C from the primary strand B, so that the fuel strand F hybridized with the primary strand B is released into the surrounding liquid and the target nucleic acid sequence C is released for further unloading steps (step V, see also FIG. 4, right side)). At the end of the reaction cycle, P remains as a single-stranded product, and C is released to enable multiple turnover.

With the catalytic replacement scheme of FIGS. 3-4, the sensitivity of the sensor device 100 is improved at the molecular level, wherein each molecule of the detection target effects the release of multiple molecules from multi-stranded precursor complexes. Previous characterizations of similar catalysis systems reported catalytic speedup of over 104 and maximum turnover of about 100. See, Zhang, D. Y. et al., Science 318, 1121-1125 (2007) and Zhang, D. Y. et al., Nucleic Acids Res. 38, 4182-4197 (2010). Using polyacrylamide gel electrophoresis (PAGE), the inventors have verified that the specific sequences used for the inventive integrated WGM system behaves qualitatively similarly in bulk solution.

The size of S and B are independent of that of C; designs that utilize larger S and B molecules could thus result in higher mass unloading and provide improved sensitivity. In tested designs, S is 20 nucleotides (nt) and B is 49 nt, compared to C being 22 nt (see table). Thus, even without catalytic turnover (e. g., see FIG. 8), a 3-fold improvement in sensitivity due to the decoupling of the unloading mass to the analyte mass is expected.

Results of Practical Tests

Figure 5:
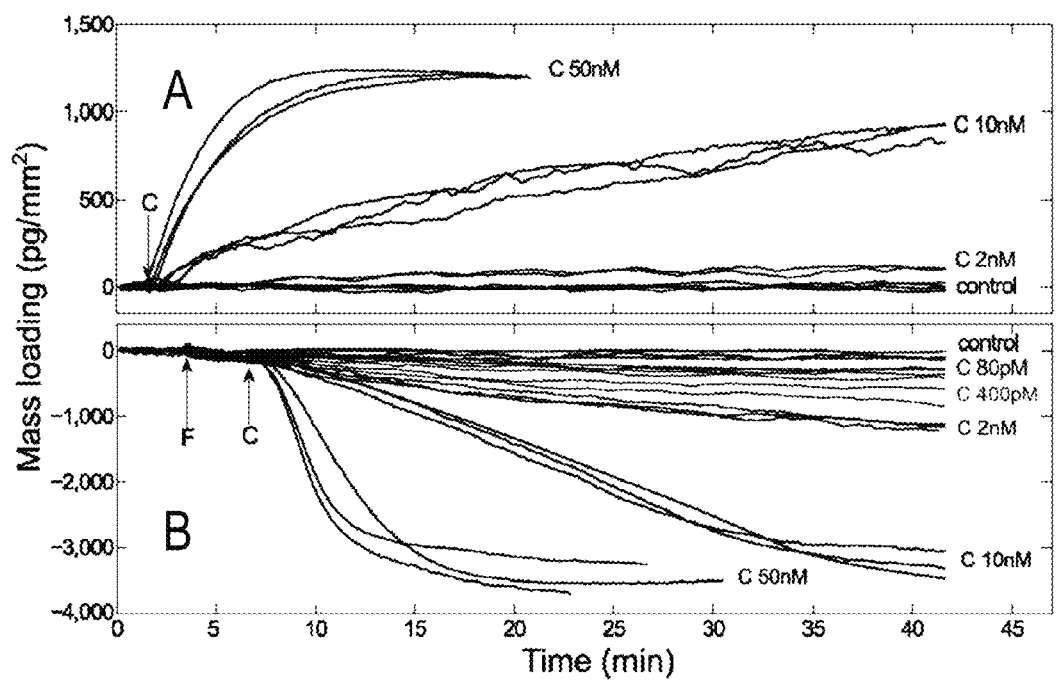
FIGS. 5 to 7 are graphical illustrations of practical results obtained with the invention (FIG. 7 discloses SEQ ID NOS 1 and 7-9, respectively, in order of appearance)

Graphs A and B of FIG. 5 illustrate a comparison of molecular sensitivity of a conventional WGM sensor versus the inventive sensor device. According to graph A of FIG. 5, with the conventional WGM sensor, a direct hybridization of target C onto the probe C* has been measured, wherein the probe C* was preattached to the microsphere surface. 4 µl of target sequence C was injected at t=200 s into the sample cell with 400 µl buffer to achieve final C concentrations of 50 nM, 10 nM or 2 nM, resp. Control experiments were done by immersing the sensors in the sample cell without injecting anything. Graph B of FIG. 5 shows a test of the inventive sensor device 100 in which target C catalytically unloads strands S and B (see FIGS. 3-4). 4 µl of F was injected at t=200 s into the sample cell with 400 µl buffer to achieve final F concentration of 400 nM. At t=400 s, 4 µl of C was injected to achieve final concentrations of 50 nM, 10 nM, 2 nM, 400 pM or 80 pM. The control trace shows the behavior of the system in the absence of C.

The results shown in graph A of FIG. 5 in terms of sensor response and timescales are consistent with previous DNA detection schemes using label-free WGM biosensors and direct hybridization. See, Vollmer, F. et al., Biophys. J. 85, 1974-1979 (2003); Suter, J. D. et al. et al., Biosens. Bioelectron. 23, 1003-1009 (2008); Scheler, O. et al., Biosens. Bioelectron. 36, 56-61 (2012); and Suter, J. D. et al., Biosens. Bioelectron. 26, 1016-1020 (2010). While the hybridization reaction could be kinetically limited, potentially by diffusion, as a benchmark for comparison against the inventive device, 40 minutes were selected as the allowed reaction time to compare molecular sensitivity.

Graph B in FIG. 5 shows the experimental results of the inventive sensor device, in which C catalytically unloads molecules from the microsphere surface. With the inventive sensor device, 400 pM concentration of analyte C produces a mass unloading signal of about 600 pg/mm2 within 40 minutes, six times as high as the mass loading yielded by 2 nM of C in the conventional hybridization-based WGM sensor. Consequently, a 30-fold improved sensitivity can be expected. Experimentally, a reliable detection of ~80 pM for 22-mer oligonucleotides has been shown, corresponding to at least 25-fold sensitivity improvement over the conventional WGM biosensor. At 80 pM concentration, there is less than 32 fmol of the DNA analyte in the droplet cell, setting a new sensitivity record for label-free microcavity biosensors. See, Vollmer, F. et al., Nanophotonics 1, 267-291 (2012) and Qavi, A. J. et al., Angew. Chem.-Int. Edit. 49, 4608-4611 (2010).

The total mass loading for the conventional direct hybridization of target C is about 1200 pg/mm2 (FIG. 5A), while the total mass unloading for the inventive WGM catalytic network mechanism is about 3500 pg/mm2 (graph B in FIG. 5). This shows that the WGM signal is indeed proportional to the length of oligonucleotides: the loaded sequence C is 22 nt long, and the unloaded sequences S and B are 20 and 49 nt long, respectively. This also confirms that the inventive WGM sensor device is reproducibly modified with biotin-streptavidin linked oligonucleotides at surface concentrations of about 10^11 strands/mm$^2$, consistent with previous observations for the dextran surface functionalization technique. See, Vollmer, F. et al., Biophys. J. 85, 1974-1979 (2003)

Combining the 30-fold expected sensitivity improvement with the 3-fold increased mass unloading, it is expected that each molecule of C on average yielded 10 rounds of reaction turnover over the course of the 40 minutes of observed reaction. This can be quantitatively confirmed by designing an alternative version of F that does not allow multiple turnover. In this case, the kinetics of mass unloading is slowed significantly and the molecular sensitivity decreases approximately 10-fold.

Figure 6:
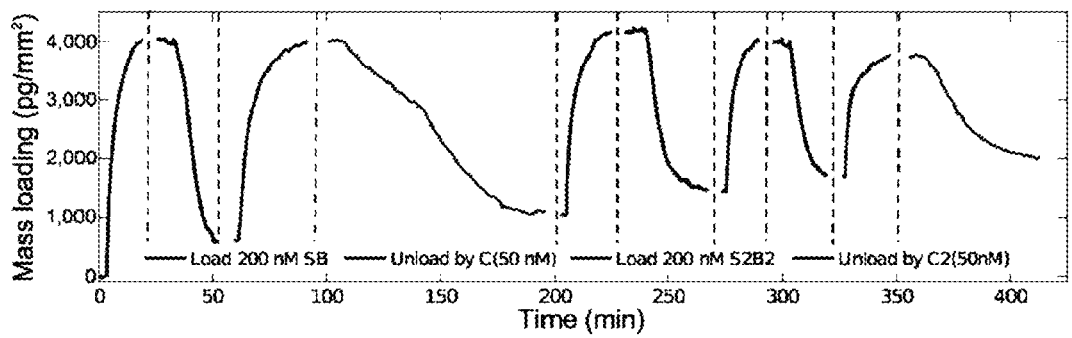

FIG. 6 illustrates repeated reuse of the inventive sensor device to detect multiple different target sequences. As shown, the same physical sensor was demonstrated to alternatingly detect 2 different nucleic acid sequences through 5 cycles of detection, showcasing both its reusability and its versatility. Loading experiments were performed with 200 nM of SB/S2B2 and unloading experiments were performed with 400 nM F/F2 and 50 nM C/C2. The mass loadings were converted from the relative shifts of each loading/unloading cycle and offset so that the next loading/unloading cycle starts where the last one ended.

The tests of FIG. 6 show that limitations in terms of versatility and reusability can be overcome with the inventive sensor device. The inventors have tested that microspheres functionalized with the same DNA sequence (P) could be used for the versatile detection of different analytes. This is feasible for the inventive sensor device because the sequence of P is independent of the sequence of the detection target C. Furthermore, it has been shown, that the same WGM microsphere can be reused. At the end of a detection reaction, the products S and FB and the analyte C are delocalized from the microsphere surface; consequently, through a mild buffer exchange the WGM can be restored to allow repeated detection cycles. FIG. 6 shows that the same WGM microsphere (functionalized with the same P molecules) can be used through 5 distinct cycles of detection to alternating detect 2 different sequences.

Figure 7:
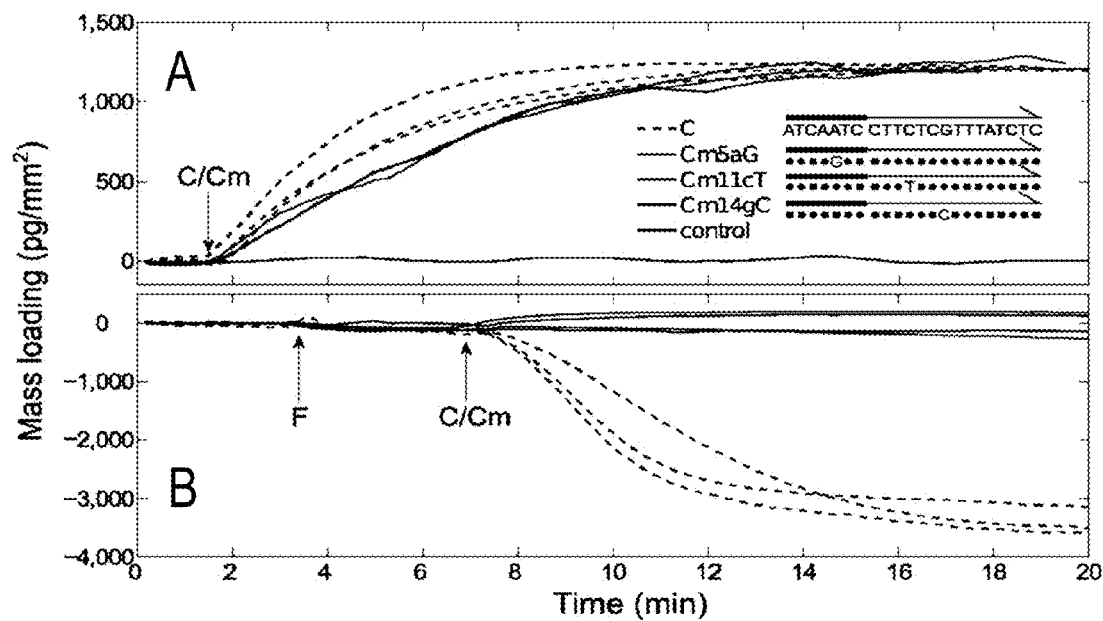

FIG. 7 illustrates a comparison of single nucleotide polymorphism (SNP) specificity of a conventional WGM sensor versus the inventive sensor device. Graph A in FIG. 7 shows the SNP detection with the conventional hybridization method. The target (dashed lines) and three SNP variants (drawn lines) were injected at t=100 sec at 50 nM concentration. The inset shows the sequences of the target and the SNP variants; the thicker line segment denotes the toehold region. Graph B in FIG. 7 shows the SNP detection with the inventive sensor device. Precursor F with a final concentration of 400 nM was injected at t=200 s and followed by the injection of target or SNP variant (C and Cms, respectively) at t=400 s to a concentration of 50 nM. Again, the target is shown with dashed lines, while the three SNP variants are shown with drawn lines.

According to graph A in FIG. 7, the conventional sensor was tested with 3 SNP variants of the intended analyte C (Cm5aG, Cm11cT, and Cm14gC). The three single base changes (A to G at position 5, C to T at position 11, G to C at position 14), were selected to be representative of the variety of both positions along the analyte sequence and of the thermodynamics of single-base changes. These SNP variants induced a similar kinetics and total amount of mass loading as the analyte C, so the standard WGM sensor is not specific to SNPs. On the contrary, according to graph B in FIG. 7, the inventive sensor device challenged by the same SNP variants is capable to sense significantly lower mass unloading by the SNP variants compared with that of the intended analyte C.

Single Replacement Scheme of Strand Displacement Reaction

For illustrating the single replacement scheme according to a further embodiment of the invention, reference is made to FIG. 8. Start step (step I) of FIG. 8 schematically shows the double-strand precursor compound BP with a primary strand B and a secondary strands P being hybridized with the primary strand B, and a target nucleic acid sequence C (analyte C) to be detected. The secondary strand P is connected via a biotin molecule L with the microsphere 11.

As with the scheme of FIG. 3, in the absence of C, BP is stably double-stranded. In the presence of the target nucleic acid sequence C, the primary strand B is delocalized from P and the surface of the microsphere 11. The secondary strand P is replaced by target nucleic acid sequence C (step I), wherein the target nucleic acid sequence C hybridized with the primary strand B is released into the surrounding liquid, while P remains as a single-stranded product at the microsphere 11 (step II). Accordingly, with the single replacement scheme, unloading of the microsphere 11 and increasing the resonance frequency thereof can be obtained as with the catalytic replacement scheme.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A sensor device comprising: an optical whispering gallery mode (WGM) resonator having a resonance frequency, wherein the WGM resonator is functionalized with a double-strand DNA precursor compound (SBP) and the resonance frequency depends on a mass load provided by the SBP, the SBP further comprising a primary strand (B), a first secondary strand (P) being hybridized with the primary strand (B) and a second secondary strand (S) being hybridized with the primary strand (B), wherein the P is connected with the WGM resonator; and the SBP is configured to replace the S by the target molecule (C); and the SBP is configured to replace the P by a further single-strand precursor compound (F) and to dissociate the B hybridized with the C and the F from the WGM resonator, wherein the mass load is decreased and the resonance frequency of the WGM resonator is increased.

2. The sensor device according to claim 1, wherein the F is configured to replace the target molecule from the B, to release C.

3. The sensor device according to claim 1, wherein the WGM resonator is provided with at least one optical waveguide or optical prism being arranged for at least one of in-coupling sample light into the WGM resonator and out-coupling resonator light out of the WGM resonator.

4. The sensor device according to claim 3, further comprising a continuous wave tunable laser source being arranged for generating the sample light.

5. The sensor device according to claim 1, further comprising: a sample cell being arranged for accommodating the WGM resonator and a sample liquid to be investigated.

6. The sensor device according to claim 1, wherein the WGM resonator has a surface layer made of a biotin streptavidin compound to which the SBP is coupled.

7. A sensing method for detecting target molecules including nucleic acid sequences, comprising: providing the sensor device of claim 1 contacting a sample liquid to be investigated with the WGM resonator; monitoring the resonance frequency of the WGM resonator; and detecting the target molecules if the resonance frequency of the WGM resonator is increased.

* * * * *

```
                              SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atcaatcctt ctcgtttatc tc                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Biotin

<400> SEQUENCE: 2
gagataaacg agaaggattg at                                              22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cttctcgttt atctcctgta                                                 20

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcgatgggta agaactttag tgtacaggag ataaacgaga aggattgat                 49

<210> SEQ ID NO 5
<211> LENGTH: 36
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 5
cttctcgttt atctcctgta cactaaagtt cttacc                                   36

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Biotin

<400> SEQUENCE: 6
cactaaagtt cttacccatc g                                                   21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atcagtcctt ctcgtttatc tc                                                  22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atcaatcctt ttcgtttatc tc                                                  22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atcaatcctt ctcctttatc tc                                                  22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctgtacacta aagttcttac c                                                   21

<210> SEQ ID NO 11
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 11
tgtaacagca actccatgtg ga                                                    22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcaactccat gtggactgta                                                       20

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcgatgggta agaactttag tgtacagtcc acatggagtt gctgttaca                       49

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcaactccat gtggactgta cactaaagtt cttacc                                     36

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccctatagtg agtcgtatta at                                                    22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Biotin

<400> SEQUENCE: 16
attaatacga ctcactatag gg                                                    22
```